(12) United States Patent
Nagami et al.

(10) Patent No.: US 6,511,466 B1
(45) Date of Patent: Jan. 28, 2003

(54) PRESSURE-SENSITIVE ADHESIVE TAPE, DISPOSABLE DIAPER USING THE SAME AND STRUCTURE FOR ATTACHING A TAPE TO THE CHASSIS OF A DISPOSABLE DIAPER

(75) Inventors: Hiroshi Nagami, Osaka (JP); Toshio Tamura, Osaka (JP)

(73) Assignee: Nitto Denko Corporation, Osaka (JP)

( * ) Notice: Subject to any disclaimer, the term of this patent is extended or adjusted under 35 U.S.C. 154(b) by 7 days.

(21) Appl. No.: 09/684,785

(22) Filed: Oct. 10, 2000

(30) Foreign Application Priority Data

Oct. 13, 1999 (JP) ............................. 11-290892
Aug. 8, 2000 (JP) ........................ 2000-239791

(51) Int. Cl.[7] ............................. A61F 13/15; B05D 5/10
(52) U.S. Cl. ................................... 604/389; 427/208.4
(58) Field of Search ............................... 604/365, 389, 604/390, 385.01; 427/208, 208.4, 208.8; 156/66, 314, 315, 331.1, 327; 428/343

(56) References Cited

U.S. PATENT DOCUMENTS 3,797,495 A * 3/1974 Schmidt ............... 427/208.4
4,136,699 A * 1/1979 Collins et al. ........ 428/355 BL
5,851,205 A * 12/1998 Hisada et al. ............... 604/389
6,001,471 A * 12/1999 Bries et al. ............... 248/205.3

FOREIGN PATENT DOCUMENTS

| JP | 05017728 A | 1/1993 |
| JP | 05247419 A | 9/1993 |
| JP | 10168399 A | 6/1998 |

* cited by examiner

*Primary Examiner*—Aaron J. Lewis
*Assistant Examiner*—Jamisue A. Webb
(74) *Attorney, Agent, or Firm*—Sughrue Mion, PLLC

(57) ABSTRACT

A pressure-sensitive adhesive tape comprising a substrate having thereon at least two different kinds of pressure-sensitive adhesive layers, wherein one pressure-sensitive adhesive layer (A) is constituted by a pressure-sensitive adhesive having a modulus at 50% elongation of 68,650 to 117,680 Pa and a modulus at 200% elongation of 147,100 to 245,170 Pa and another pressure-sensitive adhesive layer (B) is constituted by a pressure-sensitive adhesive having a modulus at 50% elongation of 19,610 to 68,650 Pa and a modulus at 200% elongation of 68,650 to 147,100 Pa. The pressure-sensitive adhesive tape has strong adhesion and suitable releasable properties. Use of such a tape in disposable diapers suppresses generation of discordant peeling sounds.

8 Claims, 4 Drawing Sheets

PRESSURE-SENSITIVE ADHESIVE TAPE, DISPOSABLE DIAPER USING THE SAME AND STRUCTURE FOR ATTACHING A TAPE TO THE CHASSIS OF A DISPOSABLE DIAPER

BACKGROUND OF THE INVENTION

1. Field of the Invention

The present invention relates to a pressure-sensitive adhesive tape for use in various types of fastening such as fastening of hygienic goods such as diapers, fixing of cloths, binding of various articles, etc. and more particularly to a pressure-sensitive adhesive tape having two or more different pressure-sensitive adhesive layers. The present invention also relates to a pressure-sensitive adhesive tape for disposable diapers using such a type of pressure-sensitive adhesive tape and to a disposable diaper having such a pressure-sensitive adhesive tape. Furthermore, the present invention relates to a structure for attaching a fastening tape comprising a pressure-sensitive adhesive tape with two or more different pressure-sensitive adhesive layers together with a release tape to a disposable diaper.

2. Description of the Related Art

Various persons including babies and young infants generally use hygienic goods such as disposable diapers. Hygienic goods use a pressure-sensitive adhesive tape as one of constituent materials. In the case of disposable diapers, pressure-sensitive adhesive tapes are used to fasten the diaper to the wearer or compacting and disposing the diaper after its use.

In the case of disposable diapers, one end of the fastening tape is applied to the rear portion of the chassis (back body) of a diaper. Application of the other end of the fastening tape to a frontal tape fixed to the front portion of the chassis (front body) of diaper makes the disposable diaper to be fastened to the body of a wearer. After its use, peeling off the other end of the fastening tape from the frontal tape releases the fixing of the disposable diaper to the body of wearer. On the pressure-sensitive adhesive layer of the other end of the pressure-sensitive adhesive tape, usually a release tape is temporarily applied in order to protect the pressure-sensitive adhesive layer until its use. In other words, disposable diapers each comprise a plurality of tapes, for example, a fastening tape for fixing the disposable diaper to the body of a wearer, a release tape, a frontal tape for releasably applying the fastening tape.

For example, JP-A-10-168399 (JP-A means unexamined published patent application) discloses pressure-sensitive adhesive sheets comprising a substrate with two pressure-sensitive adhesive layers, one pressure-sensitive adhesive layer is a pressure-sensitive adhesive layer which is non-adhesive or slightly adhesive at room temperature composed mainly of a polymer having a specified polycarbonate structure and showing a peeling power between pressure-sensitive adhesive surfaces being 100 to 2000 g/20 mm width initially and after 24 hours, and the other pressure-sensitive adhesive layer composed mainly of a polymer which is different from the polymer constituting the one pressure-sensitive adhesive layer. JP-A-5-247419 discloses a structure of a peeling portion whose interface is constituted by a pressure-sensitive adhesive layer and a release coated layer, in which the pressure-sensitive adhesive layer comprises a rubber- or acrylic-based pressure-sensitive adhesive composition and has a 100% modulus measured under the following tensile test conditions is 1.5 kg/cm$^2$ or less in the case of the rubber-based pressure-sensitive adhesive composition or 1.0 kg/cm$^2$ or less in the case of the acrylic-based pressure-sensitive adhesive composition:

Measurement Conditions:

(1) Test piece Thickness 200±10 μm, cross-section 1 mm$^2$; length of specimen between grips 10 mm;

(2) Measurement conditions: Temperature: 20° C., elongation rate: 50 mm/min.

Recently, higher quality disposable diapers are being developed and it is a trend to try to switch the material of disposable diapers to nonwoven fabrics, which have less stimulation to the skin of the wearer, are soft to the skin, have good touch and give a high grade sense.

Figure 8:
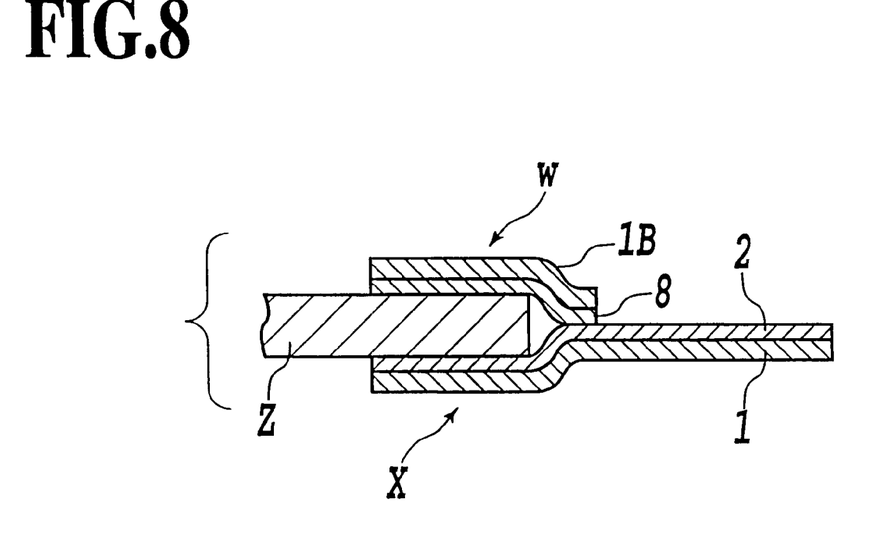
FIG. 8 is a cross-sectional view illustrating a conventional structure for attaching a fastening tape and a release tape to the chassis of a disposable diaper.

However, nonwoven fabrics are porous and difficult to secure sufficient adhesion area as compared with plastic films. Therefore, when in use as a back sheet of a disposable diaper, the fastening tape cannot cope with the shearing force applied on the fastening tape so that the fastening tape cannot be sufficiently adhered and fixed to the back sheet. As shown in FIG. 8, which is a schematic cross-sectional view showing a conventional structure for attaching fastening and release tapes to the chassis of a disposable diaper, it has been contemplated to reinforce the adhesion and fixing of a fastening tape X and a release tape W to a pressure-sensitive adhesive layer 2 on a pressure-sensitive adhesive tape backing 1 and a pressure-sensitive adhesive layer 8 on a pressure-sensitive adhesive tape substrate 1B, respectively, by overlapping the pressure-sensitive adhesive layers 2 and 8 by about 5 mm to contact each other. However, this involves a partially superimposed structure, which gives hard touch upon use. On the other hand, if the adhesive strength of the adhesive layer is increased too much, the applied fastening tape itself sometimes tends to peel off the surface of the back sheet. This is the case particularly when fastening tapes of the type which can decrease peeling sounds are selected. Therefore, pressure-sensitive adhesive tapes are being desired, which overcomes the problems of decreasing peeling sounds generated when the adhesion between the fastening tape and frontal tape is released and of realizing strong adhesion and fixing therebetween.

SUMMARY OF THE INVENTION

Under the circumstances, the present invention has been made.

An object of the present invention is to provide a pressure-sensitive adhesive tape having strong adhesion to a backsheet of a disposal diaper, etc. and an appropriate re-releasing function from a frontal tape, etc.

Furthermore, another object of the present invention is to provide a pressure-sensitive adhesive tape which can suppress generation of peeling sounds, which is uncomfortable, upon releasing the fastening tape from the frontal tape. Still another object of the present invention is to provide a pressure-sensitive adhesive tape for disposable diapers using such a type of pressure-sensitive adhesive tape.

Yet another object of the present invention is to provide a disposable diaper having such a pressure-sensitive adhesive tape.

Furthermore, an object of the present invention is to provide a structure for attaching a fastening tape comprising a pressure-sensitive adhesive tape with two or more different pressure-sensitive adhesive layers and a release tape to a disposable diaper.

The present inventors have made extensive research with view to obviate the above problems and as a result they have found that provision of at least two different kinds of pressure-sensitive adhesive layers on the substrate of a pressure-sensitive adhesive tape and setting the moduli at 50% elongation and 200% elongation of the pressure-sensitive adhesives constituting the respective pressure-sensitive adhesive layers to specified values can give rise to a pressure-sensitive adhesive tape having strong adhesion and fixation to a back-sheet comprising nonwoven fabric and at the same time decrease peeling sounds upon releasing the fastening tape from the frontal tape. The present invention has been achieved based on this discovery.

That is, the pressure-sensitive adhesive tape of the present invention comprises a substrate having thereon at least two different kinds of pressure-sensitive adhesive layers, wherein one pressure-sensitive adhesive layer (A) is constituted by a pressure-sensitive adhesive having a modulus at 50% elongation of 68, 650 to 117, 680 Pa and a modulus at 200% elongation of 147,100 to 245,170 Pa and another pressure-sensitive adhesive layer (B) is constituted by a pressure-sensitive adhesive having a modulus at 50% elongation of 19, 610 to 68,650 Pa and a modulus at 200% elongation of 68,650 to 147,100 Pa.

Here, the pressure-sensitive adhesive constituting the pressure-sensitive adhesive layer (A) may comprise a pressure-sensitive adhesive comprising 100 parts by weight of styrene block copolymer, 5 to 30 parts by weight of a softener which is liquid at a normal temperature (23° C.), 110 to 200 parts by weight of a tackifier which is solid at a normal temperature (23° C.) and the pressure-sensitive adhesive constituting the pressure-sensitive adhesive layer (B) may comprise 100 parts by weight of styrene block copolymer, 20 to 50 parts by weight of a softener which is liquid at a normal temperature, and 60 to 105 parts by weight of a tackifier which is solid at a normal temperature (23° C.).

The adherend on which the pressure-sensitive adhesive layer (A) is adhered may be non-woven fabric.

The pressure-sensitive adhesive layers (A) and (B) may have a gap of 0.1 to 15 mm therebetween.

Any of the above pressure-sensitive adhesives may be used in disposable diapers.

The disposable diaper of the present invention comprises any of the above pressure-sensitive adhesive tape.

In another embodiment, the disposable diaper of the present invention comprises a fastening tape and a release tape, wherein the fastening tape comprises any of the above pressure-sensitive adhesive tape having a pressure-sensitive adhesive layer (A), which is adhered and fixed to a back-sheet of the chassis of the disposable diaper and wherein the release tape having on one surface a pressure-sensitive adhesive layer is fixed to the chassis of the disposable diaper with the pressure-sensitive adhesive layer of the release tape being not in contact with the fastening tape, and wherein another pressure-sensitive layer (B) of the fastening tape is able to be releasably attached to the opposite surface of the release tape.

The structure for attaching a tape to the chassis of a disposable diaper according to the present invention is a structure for attaching a fastening tape and a release tape to the chassis of a disposable diaper, wherein the fastening tape comprises any of the above tapes and the pressure-sensitive adhesive layer of the fastening tape and the pressure-sensitive adhesive layer of the release tape do not contact each other.

The pressure-sensitive adhesive tape of the present invention comprises a backing and two or more different pressure-sensitive adhesive layers on one surface of the backing. For example, it exhibits excellent effects on an adherend having a portion which adheres strongly and a portion which adheres releasably, such as the fastening tape in a disposable diaper. However, its use is not limited to disposable diapers and may be effectively used where an adherend consisting of two or more materials is to be fixed or in some other cases.

The above and other objects, effects, features and advantages of the present invention will become more apparent from the following description of preferred embodiments with reference to the attached drawings.

DESCRIPTION OF PREFERRED EMBODIMENTS

Hereinafter, the pressure-sensitive adhesive tape, the structure for attaching a tape to the chassis of a disposable diaper, and disposable diaper according to the present invention will be described specifically with reference to the attached drawings.

In FIGS. 1 to 7, the same reference numerals indicate the same or like materials or parts.

Figure 1:
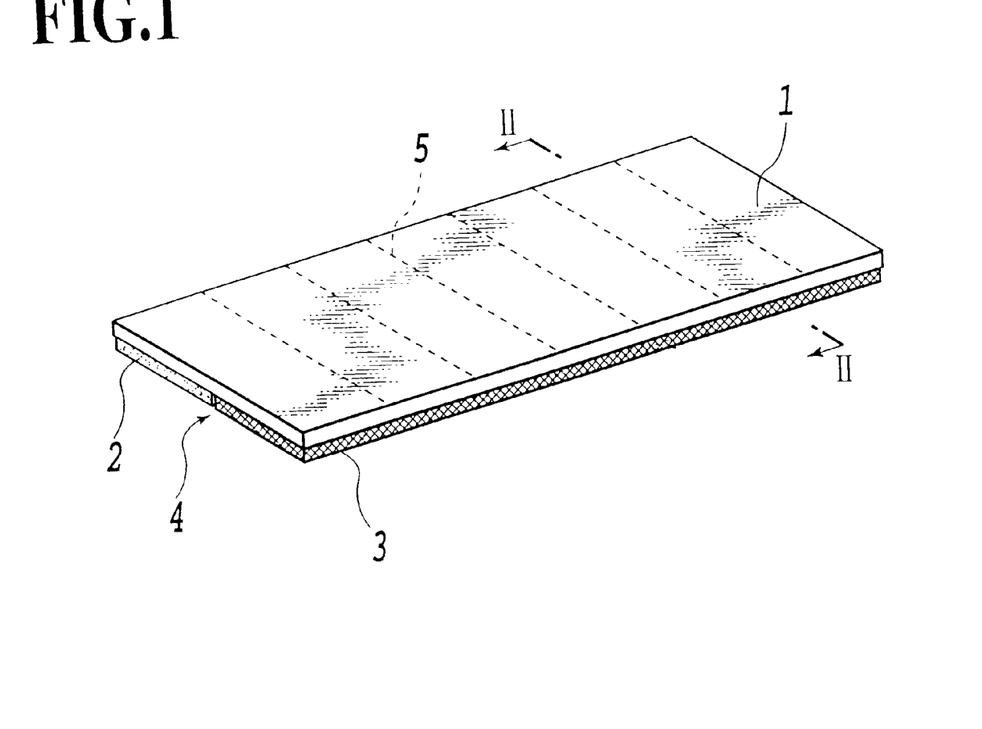
FIG. 1 is a perspective view showing a pressure-sensitive adhesive tape for use in disposable diapers according to an embodiment of the present invention.
Figure 2:
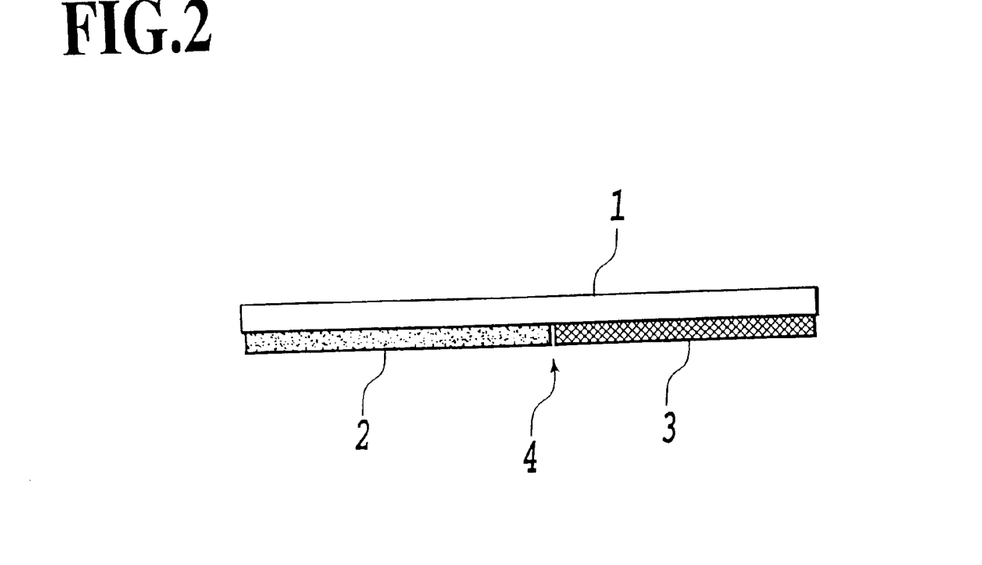
FIG. 2 is a cross-sectional view of the pressure-sensitive adhesive tape shown in FIG. 1 along the line II—II.

In FIGS. 1 and 2, a backing 1 of a pressure-sensitive adhesive tape (hereinafter, sometimes simply referred to as "backing 1") has on one surface thereof two different pressure-sensitive adhesive layers 2 and 3 side by side. For example, the pressure-sensitive adhesive layers 2 and 3 may be set to be a pressure-sensitive adhesive layer (A) and a pressure-sensitive adhesive layer (B), respectively, referred to hereinbelow. A gap 4 may be formed between the pressure-sensitive adhesive layers 2 and 3 as shown in FIG. 2. The gap 4, that is the width of the region where no pressure-sensitive adhesive is provided is preferably 0.1 to 15 mm and more preferably 0.1 to 10 mm. If the gap 4 is greater than 15 mm, the pressure-sensitive adhesive tape coated with a pressure-sensitive adhesive tends to be deformed with time when it is wound in the form of a roll, thus giving an unacceptable appearance.

As shown in FIG. 1, provision of perforations in a portion indicated by dashed line 5 in the backing 1 enables users to cut the pressure-sensitive adhesive tape along the perforations and apply the pressure-sensitive adhesive layers 2 and 3 to suitable portions of the back-sheet and frontal tape, respectively so that the tape can be effectively fixed. In the absence of perforations, the pressure-sensitive adhesive tape of the present invention may be cut to a suitable size (for example, at portions indicated by the dashed line during its production process before it can be used. On the surface of the pressure-sensitive adhesive layer, a tape for temporary application (for example, a release tape) may be provided, if desired.

In the present invention, the pressure-sensitive adhesive which constitutes the pressure-sensitive adhesive layer (A) has a modulus at 50% elongation of 68,650 to 117,680 Pa and a modulus at 200% elongation of 147,100 to 245,170 Pa.

If the moduli of the pressure-sensitive adhesive of the pressure-sensitive adhesive layer (A) are set to the above ranges, a practically satisfactory adhesive strength of the pressure-sensitive adhesive tape to the back-sheet of a disposable diaper is obtained even when non-woven fabric is used as the back-sheet of the disposable diaper. If the moduli are outside the above ranges, no suitable adhesive strength to the non-woven fabric back sheet can be obtained. The moduli of the pressure-sensitive adhesive of the pressure-sensitive adhesive layer (A) preferably has a modulus at 50% elongation of 78,450 to 117,680 Pa and a modulus at 200% elongation of 166,710 to 225,550 Pa.

In the present invention, the pressure-sensitive adhesive which constitutes the pressure-sensitive adhesive layer (B) has a modulus at 50% elongation of 19, 610 to 68, 650 Pa and a modulus at 200% elongation of 68,650 to 147,100 Pa.

If the moduli of the pressure-sensitive adhesive of the pressure-sensitive adhesive layer (B) are set to the above ranges, unexpected release of the fastening tape after bonding and fixing of the pressure-sensitive adhesive layer (B) to the frontal tape will not occur while the disposable diaper is worn. Also, when the pressure-sensitive adhesive layer (B) is to be released from the frontal tape for disposing the diaper after it was used, it can be released smoothly in such a state that the generation of discordant sounds is suppressed. On the other hand, if the moduli are outside the above ranges, no suitable adhesive strength to the non-woven fabric back sheet can be obtained. The moduli of the pressure-sensitive adhesive of the pressure-sensitive adhesive layer (B) preferably has a modulus at 50% elongation of 29,420 to 58,840 Pa and a modulus at 200% elongation of 68,650 to 107,870 Pa.

The pressure-sensitive adhesives for use in the pressure-sensitive adhesive layers (A) and (B) are not particularly limited as far as the above modulus properties are satisfied and various pressure-sensitive adhesives, for example, rubber-based pressure-sensitive adhesives, acrylic-based pressure-sensitive adhesives, silicone-based pressure-sensitive adhesive, etc. can be used.

In the present invention, it is preferred to use particularly those pressure-sensitive adhesives which contain as a major component (main polymer) styrene-based block copolymers selected from styrene-isoprene-styrene block copolymers (SIS), styrene-butadiene-styrene block copolymers (SBS), and styrene-ethylene/butylene-styrene block copolymers (SEBS).

When the above-described styrene-based block copolymers are used as a main component of the pressure-sensitive adhesive, the pressure-sensitive adhesive used in the pressure-sensitive adhesive layer (A) preferably is a pressure-sensitive adhesive comprising 100 parts by weight of styrene block copolymer, 5 to 30 parts by weight, more preferably 10 to 25 parts by weight of a softener which is liquid at a normal temperature (23° C.), 110 to 200 parts by weight of a tackifier which is solid at a normal temperature (23° C.) On the other hand, the pressure-sensitive adhesive used in the pressure-sensitive adhesive layer (B) preferably is a pressure-sensitive adhesive comprising 100 parts by weight of styrene block copolymer, 20 to 50 parts by weight, more preferably 30 to 50 parts by weight, of a softener which is liquid at a normal temperature (23° C.), and 60 to 105 parts by weight, more preferably 70 to 100 parts by weight, of a tackifier which is solid at a normal temperature (23° C.)

As the above-described softener, there can be used, for example, paraffin-based process oils, various types of liquid rubbers, vegetable oils, dibasic acidesters, liquid tackifiers. The above tackifier includes rosin-based resins, terpene-based resins, aliphatic petroleum resins, aromatic petroleum resins, coumarone-indene resins, etc.

The pressure-sensitive adhesive may contain other components, for example, antioxidants, fillers, pigments, etc. besides the above-described components.

The moduli of the pressure-sensitive adhesive used in the present invention can be adjusted by selection of main polymers which constitute the pressure-sensitive adhesive, types and blending amounts of additives, presence or absence of crosslinking in the polymers in the pressure-sensitive adhesive, and so on.

Taking into consideration the possibility of using the pressure-sensitive adhesive without solvents, it is preferred to use a pressure-sensitive adhesive comprising a styrene-based block copolymer such as SIS, SBS or SEBS as a major component and additives such as a tackifier, a softener, and an antioxidant. In this case, the adjustment of moduli can be made also by selection of main polymers which constitute the pressure-sensitive adhesive, types and blending amounts of additives, presence or absence of crosslinking in the polymers in the pressure-sensitive adhesive, and so on.

The backing of the pressure-sensitive adhesive tape used in the present invention includes, for example, plastic films such as polyethylene films, polypropylene films, films of blends of polyethylene and polypropylene, ethylene-α-olefin copolymer films, polyester films, laminated films of different plastic films, laminated backing made of plastic film and non-woven fabric, etc. However, the backing of the pressure-sensitive adhesive tape used in the present invention is not limited to these.

The thickness of the backing is not particularly limited and may be selected appropriately depending on the purpose. In the case of disposable diapers, the pressure-sensitive adhesive tape has a thickness of usually 30 to 300 μm, preferably 60 to 150 μm. When its thickness is within the above range, the pressure-sensitive adhesive tape has sufficient strength and flexibility so that this thickness range is preferred.

The pressure-sensitive adhesive tape of the present invention comprises a backing and at least the pressure-sensitive adhesive layers (A) and (B) on a surface of the backing. An additional pressure-sensitive adhesive layer may be provided.

In the present invention, the shapes of the pressure-sensitive adhesive layers (A) and (B) may be selected appropriately depending on the purpose. For example, they may be defined by straight lines, e.g., rectangular, as shown in FIG. 1, or they may be meandering such as undulant. Alternatively, they may have a doughnut shape in which the pressure-sensitive adhesive layer (A) of a circular shape is surrounded by the pressure-sensitive adhesive layer (B). Also, the backing of the pressure-sensitive adhesive tape may be provided with the pressure-sensitive adhesive layers (A) and (B) on both surfaces thereof.

The pressure-sensitive adhesive tape of the present invention may be used advantageously as a fastening tape for use in disposable diapers with a back sheet made of a non-woven fabric. However, it is not limited thereto and it may be used as a pressure-sensitive adhesive tape for various fixing purposes as required for disposable diapers, such as release tapes, frontal tapes, and tapes for disposal. Besides the use in disposable diapers, the pressure-sensitive adhesive tape of the present invention may be used as a pressure-sensitive adhesive tape for flank sweat pads. In this case, the pressure-sensitive adhesive layer (A) provided on the rear surface of the pressure-sensitive adhesive tape may serve as the adhesive portion to the non-woven pad portion and the pressure-sensitive adhesive layer (B) provided on the front surface of the pressure-sensitive adhesive tape may serve as the adhesive portion to the cloths, etc.

Hereafter, the pressure-sensitive adhesive tape of the present invention as applied to a fastening tape of a disposable diaper with a non-woven fabric back sheet will be described with reference to FIGS. 3 to 7.

Figure 3:
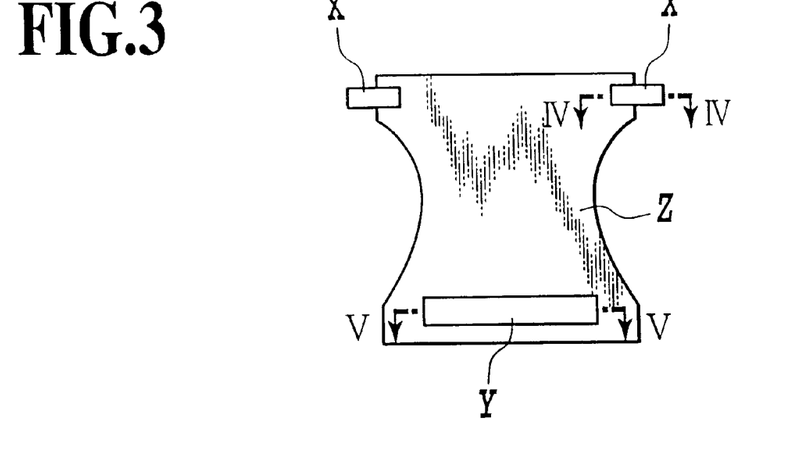
FIG. 3 is a rear view showing a disposable diaper to which the pressure-sensitive adhesive tape of the present invention is applied.
Figure 4:
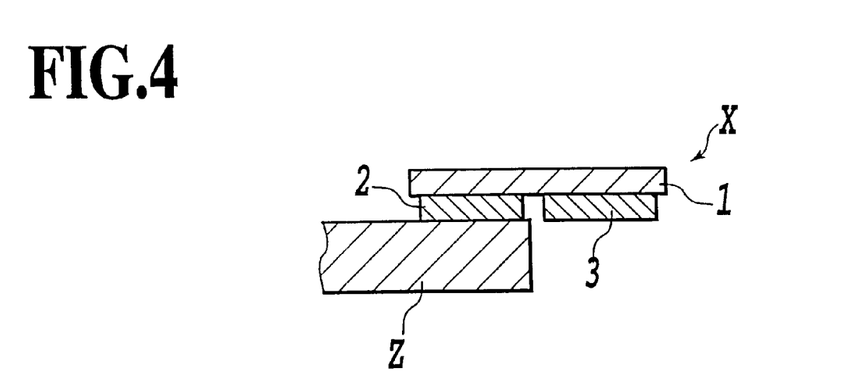
FIG. 4 is a cross-sectional view taken along the line IV—IV in FIG. 3, showing the structure of a fastening tape.
Figure 5:
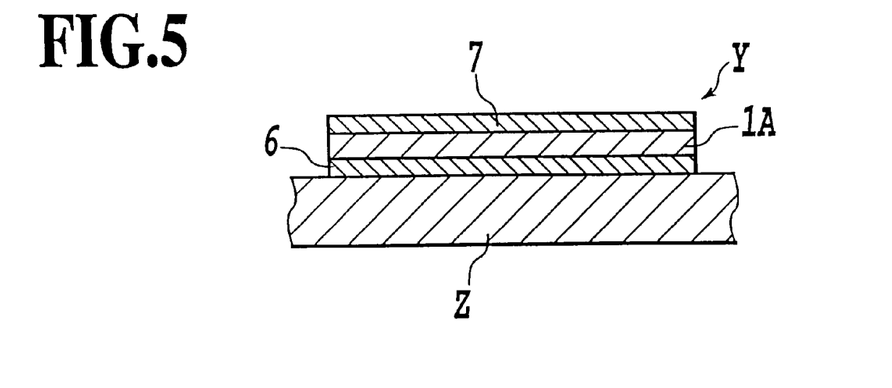
FIG. 5 is a cross-sectional view taken along the line V—V in FIG. 3, showing the structure of a frontal tape.
Figure 6:
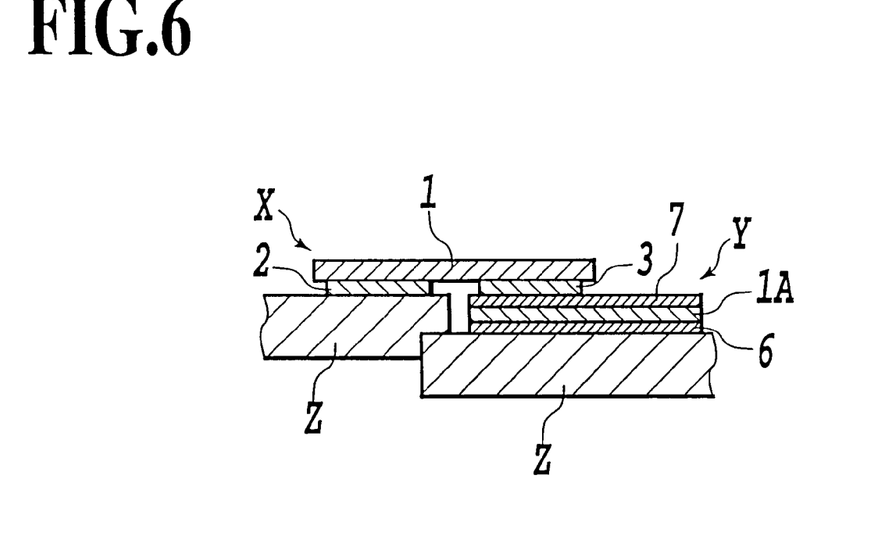
FIG. 6 is a schematic cross-sectional view showing a structure for attaching a tape to the chassis of a disposable diaper by bonding a fastening tape to a frontal tape to fix the disposable diaper to the body of the wearer.

In FIG. 3, a chassis Z of a disposable diaper is provided with a pair of fastening tapes X and X at a back body portion thereof and with a frontal tape Y in at a front body thereof. The fastening tapes X and X are each a pressure-sensitive adhesive tape on one surface of which are provided two kinds of pressure-sensitive adhesive layers (A) and (B) and are attached to the chassis of a disposable diaper through a pressure-sensitive adhesive layer 2 (pressure-sensitive adhesive layer (A)) as shown in FIG. 4. As shown in FIG. 5, the frontal tape Y comprises a backing 1A having on one surface thereof a pressure-sensitive adhesive layer 6 with a sufficient adhesive strength to the chassis of a disposable diaper and on the opposite surface thereof a release agent layer 7 which can be releasably attached to or re-attachably released from the a pressure-sensitive layer 3 (pressure-sensitive adhesive layer (B)) of the fastening tape X. As shown in FIG. 6, when the fastening tapes X and X are pressed onto the frontal tape Y, the pressure-sensitive adhesive layers 3 and 3 of he fastening tapes X and X adhere to the release agent layer 7 of the frontal tape Y to achieve the object of equipping and fixing the disposable diaper to the user's body. The thicknesses of the pressure-sensitive adhesive layers 2 and 3 of the fastening tape X are not particularly limited and usually they may be in the rage of 20 to 100 $\mu$m and preferably in the range of 30 to 70 $\mu$m. The thicknesses of the pressure-sensitive adhesive layers of the fastening tape within the above ranges are preferred since sufficient adhesive strength can be obtained.

As the material of the backing 1A of the frontal tape Y, any of the materials which can be used in the backing 1 of the fastening tape X may be used. The backing 1A of the frontal tape Y may be made of the same material as or different from that of the backing 1 of the fastening tape X. The thickness of the backing 1A of the frontal tape is 10 to 100 $\mu$m, preferably 15 to 50 $\mu$m. The thickness of the backing of the frontal tape within the above range is preferred since the disposal diaper will not lose flexibility and the effect of reinforcing the application of the fastening tape to the chassis Z of the disposable diaper can be obtained sufficiently. As the frontal tape, there may be used, for example, one which includes a polypropylene film on one surface of which is coated with a silicone release agent containing three-dimensional organopolysiloxane that has a sounding-deadening effect and high retention property such that the tape will not be detached as one described in Unexamined Published Japanese Patent Application No. Hei 5-17728. In an embodiment, the pressure-sensitive adhesive layer 2 (pressure-sensitive adhesive layer (A)) may be used as the pressure-sensitive adhesive layer 6. In this case, the thickness of the pressure-sensitive adhesive layer of the frontal tape Y is not particularly limited but it is usually 4 to 30 $\mu$m and preferably 5 to 20 $\mu$m. The thickness of the pressure-sensitive adhesive layer of the frontal tape within the above range is preferred since sufficient adhesive strength can be obtained.

The fastening tape X can be attached to the chassis Z of a disposable diaper by temporarily applying a release tape (not shown) on a surface of the pressure-sensitive adhesive layer 3 in a state as shown in FIG. 4 in order to protect the surface of the pressure-sensitive adhesive layer until use, removing the release tape to expose the surface of the pressure-sensitive adhesive layer 3 upon and pressing the fastening tape to the frontal tape.

Figure 7A:
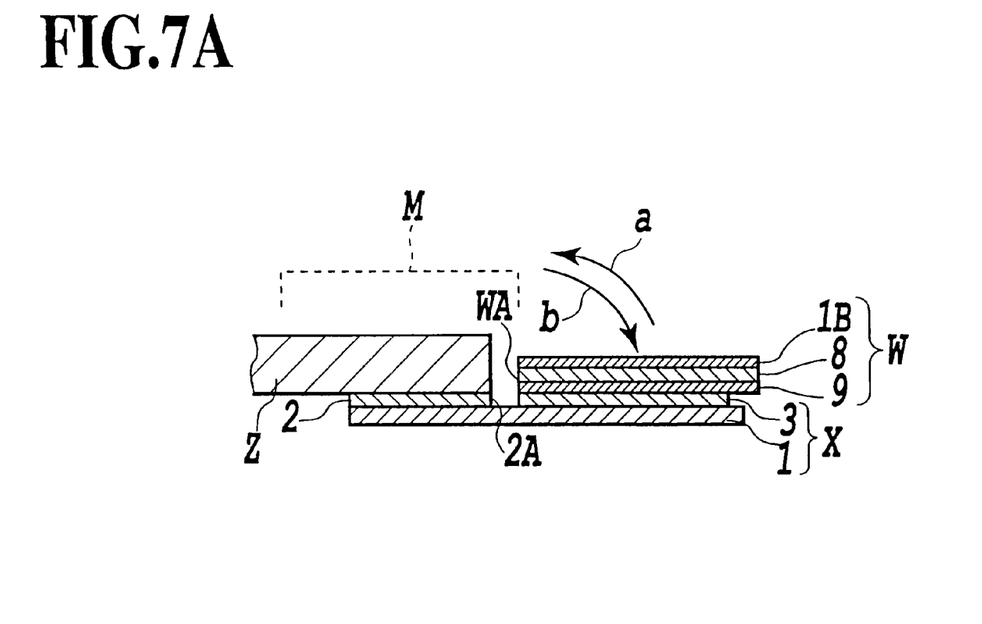
FIG. 7A is a cross-sectional view illustrating the manner in which a fastening tape and a release tape are adhered and fixed to the chassis of a disposable diaper, wherein the release tape remains to be bonded to the chassis of the disposable diaper.
Figure 7B:
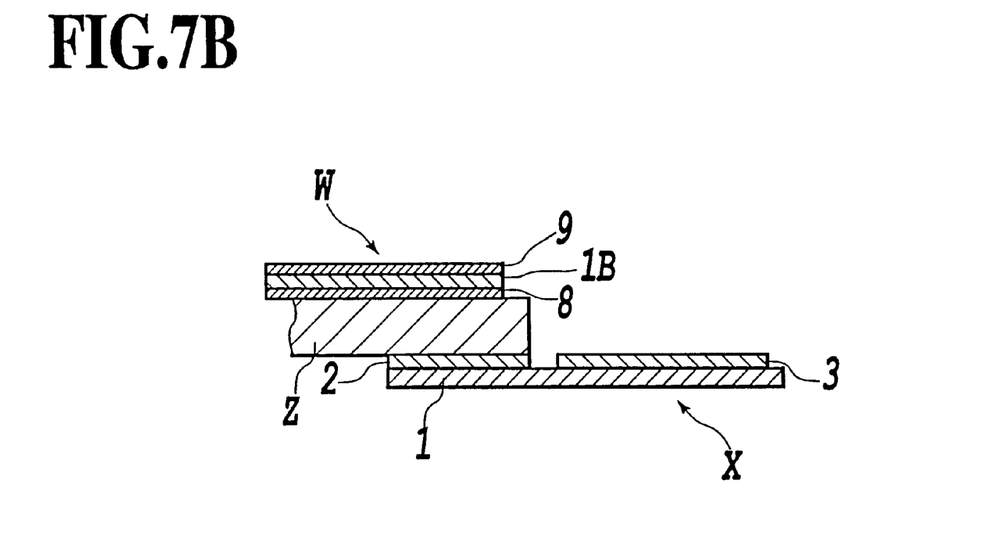
FIG. 7B is a cross-sectional view illustrating the manner in which a fastening tape and a release tape are adhered and fixed to the chassis of a disposable diaper, wherein the release tape has been bonded to the chassis of the disposable diaper.

FIG. 7 illustrates an example of attachment of a release tape W on the fastening tape X in order to increase practical workability when the above fastening tape X is to be attached to the chassis of a disposable diaper. The release tape W is, As shown in FIG. 7A, the release tape W includes a backing 1B of a pressure-sensitive adhesive tape having on one surface thereof a pressure-sensitive adhesive layer 8 with a sufficient adhesive strength to a top-sheet of the chassis of a disposable diaper and a release agent layer 9 on the opposite surface thereof. As the material of the backing 1B of the pressure-sensitive adhesive tape in the release tape W, any of the materials that are used for the backing of the pressure-sensitive adhesive tape used in the fastening tape X may be employed. The thickness of the backing 1B of the pressure-sensitive adhesive tape used in the release tape is 20 to 150 $\mu$m, preferably 30 to 100 $\mu$m. The thickness of the backing of the pressure-sensitive adhesive tape used in the release tape within the above range is preferable since the flexibility of the disposable diaper will not be lost.

In the stage of attaching the fastening tape and release tape to the disposable diaper, the release agent layer 9 is pressed onto the pressure-sensitive adhesive layer 3 of the fastening tape X to protect the pressure-sensitive adhesive layer 3 of the fastening tape X. In this state, the both tapes X and W were wholly bent toward the direction indicated by the arrow a, the resulting tape complex is applied to the chassis of the disposable diaper by means of the adhesion of the pressure-sensitive adhesive layer 8 of the release tape W to realize the state indicated dotted line M. In this case, an end $W_A$ of the release tape W on the side of the chassis Z of the disposable diaper may be provided at a distance from an end 2A of the pressure-sensitive adhesive layer 2 so that the former will not contact the latter. Usually, the distance is about 0.5 to about 5 mm.

When the disposable diaper is used, only the fastening tape X will be separated at the interface between pressure-sensitive adhesive layer 3 of the fastening tape X and the release tape W in the direction indicated by the arrow b in FIG. 7A to realize the state as shown in FIG. 7B. Application of the exposed surface of the pressure-sensitive adhesive layer 3 to the frontal tape Y as described above effect the equipment and fixing of the disposable diaper. As described above, fixing the release tape W to the chassis of the disposable diaper by fixing such that the end $W_A$ of the release tape W on the side of the chassis Z of the disposable diaper is remote from the end 2A of the pressure-sensitive adhesive layer 2 makes it possible to easily construct a structure of attaching a tape to the chassis of a disposable diaper with sufficient adhesion and fixing without resort to a conventional tape attachment structure having the structure in which the pressure-sensitive adhesive layers of the fastening tape and release tape contact each other as shown in FIG. 8. This is because use of the pressure-sensitive adhesive tape of the present invention as a fastening tape to be bonded and fixed to a back-sheet of the chassis of a disposable diaper increases the adhesive function of the back-sheet to the non-woven fabric so that the fastening tape alone can cope with the power applied to the fastening tape X in the direction of shearing. In addition, as shown in FIG. 7B, the fastening tape X and the release tape W do not bond to each other when they are fixed to the chassis of the disposable diaper. This is useful for providing satisfactory soft feeling at the attachment portion of the disposable diaper and thus is preferred.

After use or for confirming the state of the disposable diaper, the fastening tape X may be released from frontal tape and bent in the direction indicated by the arrow a to press the pressure-sensitive adhesive layer 3 of the fastening tape X to the backing 1B of the pressure-sensitive adhesive tape in the release tape W so that it can return to the state shown by dotted line M.

As stated above, the embodiment shown in FIG. 7 is a tape attachment structure of a simple construction, which includes a pressure-sensitive adhesive tape comprising a fastening tape X with a backing 1 having both pressure-sensitive adhesive layers (A) and (B) on one surface thereof and a release tape W comprising a with a backing 1B having a pressure-sensitive adhesive layer 8 with a sufficient adhesive strength to the top-sheet of the chassis of a disposable diaper on one surface thereof and a release agent layer 9 which releasably adheres to or re-attachably released from the pressure-sensitive adhesive layer 3 (pressure-sensitive adhesive layer (B) ) of the fastening tape on the opposite surface thereof. Here, the tape attachment structure is not limited to the one shown in FIG. 7 and various other tape attachment structures may be used.

Since it has be above construction, the pressure-sensitive adhesive tape of the present invention can be effectively applied to those adherends which require two or more different adhesive powers. In particular the pressure-sensitive adhesive tape of the present invention exhibits excellent effects in disposable diapers with back-sheets made of non-woven fabric. It can not only maintain sufficient adhesion and fixing function to the back-sheet and but also maintain the adhesion function to the frontal tape while the disposal diaper is being worn and increase the peeling property and decrease peeling sound upon releasing. Furthermore, according to the present invention, the adhesive function to non-woven fabric is increased and as a result the structure for attaching a complex of a fastening tape and a release tape to the chassis of a disposable diaper in order to prevent the release of the fastening tape bonded and fixed to the back-sheet is no longer necessary, so that the structure of the attachment portion for attaching the fastening tape can be simplified. As a result, a satisfactory soft feeling at the attachment portion of the disposable diaper can be provided.

EXAMPLES

Hereinafter, the pressure-sensitive adhesive tape of the present invention will be described in detail by examples. However, the present invention is not limited thereto. In the examples, all parts are by weight. As SIS, petroleum resins, process oil, and antioxidant, the following substances were used.

SIS: Trade name "Kraton D-1107", manufactured by Shell Chemical Petroleum resin: Trade name "Clearon M105", manufactured by Yasuhara Chemical; trade name "Quintone N190", manufactured by Nippon Zeon Process oil: Trade name "Shell Flex 371N", manufactured by Shell Chemical Antioxidant: Trade name "Irganox 1010", manufactured by Ciba-Geigy Example 1

A pressure-sensitive adhesive having the composition shown in Table 1 was coated on one surface of a backing (polypropylene/polyethylene blend film, 100 μm thick) of 71 mm in width to fabricate a pressure-sensitive adhesive tape having both pressure-sensitive adhesive layers (A) and (B) on one surface thereof as shown in FIG. 1. The width of pressure-sensitive adhesive (A) was 30 mm and that of pressure-sensitive adhesive (B) was 40 mm. The thickness of the coating was 50 μm for each pressure-sensitive adhesive layer. The gap between the pressure-sensitive adhesive (A) and the pressure-sensitive adhesive (B), i.e., the width of the region where no pressure-sensitive adhesive was coated, was 1 mm. The obtained pressure-sensitive adhesive tape was wound around a core (paper core of 75 mm in inner diameter and 95 mm in outer diameter) to a length of 800 m. No deformation in the shape of the obtained roll (wound article) was observed.

Example 2

A pressure-sensitive adhesive tape was fabricated in the same manner as in Example 1 except that the kinds of the pressure-sensitive adhesives used for forming the pressure-sensitive adhesive layers (A) and (B), respectively, were changed as shown in Table 1. The obtained pressure-sensitive adhesive tape was wound around a core (paper core of 75 mm in inner diameter and 95 mm in outer diameter) to a length of 800 m. No deformation in the shape of the obtained roll (wound article) was observed.

Comparative Example 1

A pressure-sensitive adhesive tape was fabricated in the same manner as in Example 1 except that the kinds of the pressure-sensitive adhesives used for forming the pressure-sensitive adhesive layers (A) and (B), respectively, were changed as shown in Table 1.

Comparative Example 2

A pressure-sensitive adhesive tape was fabricated in the same manner as in Example 1 except that no pressure-sensitive adhesive layer (A) was provided and that the same pressure-sensitive adhesive as one used for forming the pressure-sensitive adhesive layer (B) alone was coated all over one surface of the backing.

Comparative Example 3

A pressure-sensitive adhesive tape was fabricated in the same manner as in Example 1 except that no pressure-sensitive adhesive layer (B) was provided and that the same pressure-sensitive adhesive as one used for forming the pressure-sensitive adhesive layer (A) alone was coated all over one surface of the backing.

<Method for Measuring the Moduli of Pressure-sensitive Adhesives>

The pressure-sensitive adhesive layers (A) and (B) in each of the pressure-sensitive adhesive tapes in Examples 1 and 2 and Comparative Example 1 as well as the pressure-sensitive adhesive layer (B) in Comparative Example 2 and the pressure-sensitive adhesive layer in Comparative Example 3 were scraped from the backing and the pressure-sensitive adhesives alone were collected. Each of the collected pressure-sensitive adhesives was dissolved in toluene and a pressure-sensitive adhesive solution was prepared.

The obtained pressure-sensitive adhesive solution was coated on a release liner (separator) and dried to form a pressure-sensitive adhesive layer of 50 μm in thickness and 150 mm in width. Then, the pressure-sensitive adhesive layer was wound from its end in the direction of width to form a cylinder of 7.5 mm² in cross section.

The pressure-sensitive adhesive worked into cylindrical form was fixed to the chucks of a tensile tester (distance between chucks: 20 mm) and the S—S characteristic of the pressure-sensitive adhesive was measured at a tensile speed of 300 mm/minute and the results were recorded. From the recorded values, the moduli at 50% elongation and at 200% elongation, respectively, of the pressure-sensitive adhesives were obtained and converted into values in Pa units. Table 1 shows the moduli of each pressure-sensitive adhesive.

release agent containing 50% by weight of a three-dimensionalized organopolysiloxane (50 parts by weight of KS-3703 manufactured by Shin-Etsu Chemical, 50 parts by weight of KS-3800 manufactured by Shin-Etsu Chemical, and 3 parts by weight of PL-50T manufactured by Shin-Etsu Chemical) to a thickness of 1 μm was used. The adherend was fixed to a stainless steel plate when in use.

<Holding Power of Frontal Tape>

The pressure-sensitive adhesive layer (B) of each of the pressure-sensitive adhesive tapes in Examples 1 and 2 and Comparative Example 1 or each of the pressure-sensitive adhesive layers in the pressure-sensitive adhesive tapes in Comparative Examples 2 and 3 was superimposed on the same adherend as that used in the evaluation of peel adhesion from a frontal tape and pressed by a 2 kg roller so that the application area was 25 mm×25 mm, followed by standing in an atmosphere at 40° C. for 30 minutes. Thereafter, a 1 kg weight was hung on the pressure-sensitive adhesive tape, which was left in an atmosphere at 40° C., and the time in which the pressure-sensitive adhesive tape fell was measured.

<Peeling Sound Upon Peeling from a Frontal Tape>

The same adherend (frontal tape) as that used in the evaluation of peel adhesion was applied to the ventral part of a disposable diaper. The pressure-sensitive adhesive layer (B) of each of the pressure-sensitive adhesive tapes in

TABLE 1

| Pressure-sensitive adhesive composition | Example 1 Pressure-sensitive adhesive layer (A) | Example 1 Pressure-sensitive adhesive layer (B) | Example 2 Pressure-sensitive adhesive layer (A) | Example 2 Pressure-sensitive adhesive layer (B) | Comparative Example 1 Pressure-sensitive adhesive layer (A) | Comparative Example 1 Pressure-sensitive adhesive layer (B) | Comparative Example 2 Pressure-sensitive adhesive layer | Comparative Example 3 Pressure-sensitive adhesive layer |
|---|---|---|---|---|---|---|---|---|
| Kraton D1107 (part) Petroleum resin | 100 | 100 | 100 | 100 | 100 | 100 | 100 | 100 |
| Clearon M105 (part) | 150 | | 130 | | 150 | | | 150 |
| Quintone N190 (part) | | 100 | | 90 | | 120 | 100 | |
| Shell Flex 371 (part) | 20 | 20 | 20 | 40 | 20 | 20 | 20 | 20 |
| Irganox 1010 (part) | 3 | 3 | 3 | 3 | 3 | 3 | 3 | 3 |
| 50% Modulus (Pa) | 78450 | 58840 | 78450 | 49030 | 78450 | 68650 | 58840 | 78450 |
| 200% Modulus (Pa) | 176500 | 88260 | 156900 | 78450 | 176500 | 166700 | 88260 | 176500 |

Each of the pressure-sensitive adhesive tapes in Examples 1 and 2 and Comparative Examples 1 to 3 was measured of the following properties.

<Peel adhesion>

The pressure-sensitive adhesive layer (B) of each of the pressure-sensitive adhesive tapes in Examples 1 and 2 and Comparative Example 1 or each of the pressure-sensitive adhesive layers in the pressure-sensitive adhesive tapes in Comparative Examples 2 and 3 was superimposed on a surface of a release layer of the adherend described below and pressed by a reciprocating motion of a 2 kg roller thereon. After 3 minutes, the pressure-sensitive adhesive tape was peeled from the adherend at a peel speed of 30 mm/minute to perform 180° angle peel (180° peel) and the peel adhesion at that time was measured.

Adherend (frontal tape): A 25-μm thick polypropylene film coated on one surface thereof with a silicone-based Examples 1 and 2 and Comparative Example 1 or each of the pressure-sensitive adhesive layers in the pressure-sensitive adhesive tapes in Comparative Examples 2 and 3 was superimposed on an open surface of the applied frontal tape and pressed by a reciprocating movement of a 2 kg roller thereon. Immediately after the application, the pressure-sensitive adhesive tape was peeled from the frontal tape at a peel speed of 50 m/minute and peeling sound (sound pressure level) was measured using a digital sound level meter.

<Peel Adhesion from Non-woven Fabric>

A commercially available disposable diaper having a back sheet made of non-woven fabric was provided and a backsheet portion thereof was cut off. To its surface corresponding to the inside of the disposable diaper was applied a pressure-sensitive adhesive double coated tape and the resulting laminate was applied to a stainless steel to form an adherend.

The pressure-sensitive adhesive layer (B) of each of the pressure-sensitive adhesive tapes in Examples 1 and 2 and Comparative Example 1 or each of the pressure-sensitive adhesive layers in the pressure-sensitive adhesive tapes in Comparative Examples 2 and 3 was superimposed on an open surface of the non-woven fabric of the adherend and pressed by a reciprocating movement of a 2 kg roller thereon. Then, after standing it for 30 minutes, the pressure-sensitive adhesive tape was peeled at a peel speed of 300 mm/minute using a tensile tester to effect 180° peel and the peel adhesion at that time was measured.

<Holding Power for Non-woven Fabric>

The same adherend as that used in the evaluation of peel adhesion from non-woven fabric was provided. The pressure-sensitive adhesive layer (B) of each of the pressure-sensitive adhesive tapes in Examples 1 and 2 and Comparative Example 1 or each of the pressure-sensitive adhesive layers in the pressure-sensitive adhesive tapes in Comparative Examples 2 and 3 was superimposed on the adherend and pressed so that the application area was 25 mm×25 mm, followed by standing in an atmosphere at 40° C. for 30 minutes. Thereafter, a 500-g weight was hung on the pressure-sensitive adhesive tape, which was left in an atmosphere at 40° C., and the time in which the pressure-sensitive adhesive tape fell was measured.

<Evaluation by Monitors>

To a commercially available disposable diaper with a back-sheet made of non-woven fabric was applied each of the pressure-sensitive adhesive tapes of Examples 1 and 2 and Comparative Examples 1 to 3 as a fastening tape to fabricate disposable diapers and the states of the disposable diapers when they were actually used were observed by monitors. The disposable diapers of good general evaluation were indicated by a symbol "○" and those which showed problems upon use were indicated by a symbol "×".

sensitive adhesive tape occurred while the disposable diaper is being worn. On the other hand, the pressure-sensitive adhesive tapes of Comparative Examples 1 to 3 showed undesirable results when in use as shown in the results of evaluation by monitors in Table 2.

The invention may be embodied in other specific forms without departing from the spirit or essential characteristics thereof. Therefore, the present embodiment is to be considered in all respects as illustrative and not restrictive, the scope of the invention being indicated by the appended claims rather than by the foregoing description and all changes which come within the meaning and range of equivalency of the claims are therefore intended to be embraced therein.

What is claimed is:

1. A pressure-sensitive adhesive tape comprising a substrate having thereon at least two different kinds of pressure-sensitive adhesive layers, wherein a first pressure-sensitive adhesive layer (A) is constituted by a pressure-sensitive adhesive having a modulus at 50% elongation of 68,650 to 117,680 Pa and a modulus at 200% elongation of 147,100 to 245,170 Pa and a second pressure-sensitive adhesive layer (B) is constituted by a pressure-sensitive adhesive having a modulus at 50% elongation of 19,610 to 68,650 Pa and a modulus at 200% elongation of 68,650 to 147,100 Pa.

2. The pressure-sensitive adhesive tape as claimed in claim 1, wherein the pressure-sensitive adhesive constituting the first pressure-sensitive adhesive layer (A) comprises a pressure-sensitive adhesive comprising 100 parts by weight of styrene block copolymer, 5 to 30 parts by weight of a softener which is liquid at a normal temperature of 23° C., 110 to 200 parts by weight of a tackifier which is solid at a normal temperature of 23° C. and the pressure-sensitive adhesive constituting the second pressure-sensitive adhesive layer (B) comprises 100 parts by weight of styrene block copolymer, 20 to 50 parts by weight of a softener which is liquid at a normal temperature, and 60 to 105 parts by weight of a tackifier which is solid at a normal temperature of 23° C.

TABLE 2

| | Frontal tape adhesion and release side | | | Diaper chassis side | | | |
|---|---|---|---|---|---|---|---|
| | Peel adhesion from frontal tape (N/25 mm) | Holding power for frontal tape (minute) | Sound of peeling from frontal tape (dB) | Peel adhesion from non-woven fabric (N/25 mm) | Holding power for non-woven fabric (minute) | Results of evaluation by monitors | |
| Example 1 | 2.5 | 380 | 61 | 8.5 | 330 | Good | ○ |
| Example 2 | 1.9 | 260 | 60 | 7.5 | 180 | Good | ○ |
| Comparative Example 1 | 3.1 | 740 | 72 | 8.2 | 310 | Peeling sound is intense when peeling from frontal portion | × |
| Comparative Example 2 | 2.4 | 360 | 61 | 9.3 | 40 | Pressure-sensitive adhesive tape peels from the side of the chassis of diaper | × |
| Comparative Example 3 | 3.8 | 1020 | 75 | 8.5 | 280 | Peeling sound is intense when peeling from frontal portion | × |

From the results shown in Table 2, it can be seen that the pressure-sensitive adhesive tapes of Examples 1 and 2 can be peeled from the frontal tape at peel adhesion of 3N/25 mm or less and at peeling sound level of 65 dB or less, which indicates suppression of generation of discordant sounds upon peeling. The holding power for non-woven fabric is 100 minutes or more and therefore has a strong adhesion to the back-sheet and no expected peeling of the pressure- 3. The pressure-sensitive adhesive tape as claimed in claim 1 or 2, wherein an adherend on which the first pressure-sensitive adhesive layer (A) adheres is non-woven fabric.

4. The pressure-sensitive adhesive tape as claimed in any of claims 1, 2 or 3, wherein the first and second pressure-sensitive adhesive layers (A) and (B) have a gap of 0.1 to 15 mm therebetween.

5. A pressure-sensitive adhesive tape for disposable diapers, comprising a pressure-sensitive adhesive tape as claimed in any of claims 1, 2, 3 or 4.

6. A disposable diaper comprising a pressure-sensitive adhesive tape as claimed in claim 5.

7. A structure for attaching a tape to a chassis of a disposable diaper, wherein a fastening tape having a pressure-sensitive adhesive layer thereon and a release tape having a pressure sensitive adhesive layer thereon are attached to the chassis of a disposable diaper, wherein the fastening tape comprises a tape as claimed in claim 5 and the pressure-sensitive adhesive layer of the fastening tape and the pressure-sensitive adhesive layer of the release tape do not contact each other.

8. A disposable diaper comprising a fastening tape and a release tape, wherein the fastening tape comprises a pressure-sensitive adhesive tape having a first pressure-sensitive adhesive layer (A), which is adhered and fixed to a back-sheet of a chassis of the disposable diaper, said layer (A) being constituted by a pressure-sensitive adhesive having a modulus at 50% elongation of 68,650 to 117,680 Pa and a modulus at 200% elongation of 147,100 to 245,170 Pa, wherein the release tape having on one surface a pressure-sensitive adhesive layer fixed to a chassis of the disposable diaper with the pressure-sensitive adhesive layer of the release tape not being in contact with the fastening tape, and wherein a second pressure-sensitive layer (B) of the fastening tape, being constituted by a pressure-sensitive adhesive having a modulus at 50% elongation of 19,610 to 68,650 Pa and a modulus at 200% elongation of 68,650 to 147,100 Pa, is able to be releasably attached to an opposite surface of the release tape.

* * * * *